(12) United States Patent
Bhalla (10) Patent No.: US 8,278,448 B2
(45) Date of Patent: *Oct. 2, 2012

(54) TECHNETIUM AND RHENIUM COMPLEXES

(75) Inventor: Rajiv Bhalla, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/232,255

(22) Filed: Sep. 14, 2011

(65) Prior Publication Data

US 2012/0077967 A1 Mar. 29, 2012

Related U.S. Application Data

(63) Continuation of application No. 11/576,543, filed as application No. PCT/GB2005/003806 on Oct. 4, 2005, now Pat. No. 8,022,211.

(30) Foreign Application Priority Data

Oct. 4, 2004 (GB) .................................. 0421987.9

(51) Int. Cl.
*C07F 13/00* (2006.01)
(52) U.S. Cl. ................ 546/2; 534/14; 548/101
(58) Field of Classification Search ............. 534/14; 546/2; 548/101
See application file for complete search history.

(56) References Cited

U.S. PATENT DOCUMENTS

| | | | |
|---|---|---|---|
| 5,824,288 A | 10/1998 | Peng et al. | |
| 5,869,025 A | 2/1999 | Peng et al. | |
| 8,022,211 B2 * | 9/2011 | Bhalla | 546/2 |

FOREIGN PATENT DOCUMENTS

| | | |
|---|---|---|
| JP | 10-045903 | 2/1998 |
| WO | WO 03/077727 | 9/2003 |

OTHER PUBLICATIONS

Arnold et al. "Copper complexes of the functionalized tripodal ligand tris(2-pyridyl)-methylamine and its derivatives" Journal of the Chemical Society, Dalton Transactions, 2001, pp. 736-746.*

Hannon, M., et al., J. Chem. Soc., Perkin Trans., 1 (2000) 1881-1889.
Reger, D., et al., Journal of Organometallic Chemistry, 658 (2002) 50-61.
Arnold, P.J., et.al. "Copper complexes of the functionalized tripodal ligand tris(2-pyridyl)-methylamine and its derivatives" Journal of the Chemical Society. Dalton Transactions No. 5, Mar. 7, 2001, pp. 736-746.
Reger, D.L., et.al. "Syntheses and structural characterizations of rhenium carbonyl complexes of a bitopic ferrocene-linked bis (pyrazolyl) methane ligand" Journal of Organometallic Chemistry, vol. 290, no. 8 Apr. 15, 2005 pp. 1889-1900.
Reger, D.L., et.al., "Bitopic phenylene-linked bis(pyrazolyl)methane ligands: Preparation and supramolecular structures of hetero- and homobimetallic complexes incorporating organoplatinum(II) and tricarbonylrhenium(I) centers" Organometallics, vol. 24, No. 7 Mar. 28, 2005 pp. 1544-1555.
Dumez D.D., et.al., "Selective oxidation of alkyl ligand in rhenium(V) oxo complexes" Journal of the American Chemical Society, vol. 118. No. 49, Dec. 11, 1996, pp. 12416-12423.
Alberto, et.al., "A novel organometallic aqua complex of technetium for the labeling of biomolecules: Synthesis of [99mTc(0H2)3(C0)3]+ from [99mTc04]- in Aqueous Solution and its Reaction with a bifunctional ligand" Journal of the American Chemical Society, vol. 120, No. 31 Aug. 12, 1998, pp. 7987-7988.
Kothari, K.K., et.al. "Syntheses, in vitro and in vivo characterization of a ,99m.Tc-(I)-tricarbonyl-benzylamino-dihydroxymethyl phosphine (NP2) chelate" Applied Radiation and Isotopes, vol. 58, No. 5 May 2003, pp. 543-549.
Zelentsov, V.V., et. al. "Magnetic properties of tetravalent rhenium hexahalide complexes" Doklady Chemistry vol. 205, No. 5, 1972, pp. 691-693.
Akimov, V.K., et.al., "Reaction of rhenium (IV) halide complexes with pyrazolone derivatives. Extraction photometric determination of rhenium (IV) by means of diantipyrylpropylmethane" Journal of Analytical Chemistry of the USSR, vol. 25, No. 10, 1970, pp. 1665-1673.
Akimov, V.K., et.al. "Gravimetric determination of rhenium (IV) by means of antipyrine derivatives" Journal of Analytical Chemistry of the USSR, vol. 25, No. 9, 1970, pp. 1503-1505.

* cited by examiner

*Primary Examiner* — Joseph Kosack (57) ABSTRACT

Novel radioactive technetium and rhenium complexes comprising tripodal ligands are provided by the present invention. In particular, Tc(I) complexes are provided by the present invention. Novel ligands suitable for the formation of the technetium and rhenium complexes of the invention are also provided, as well as radiopharmaceutical compositions comprising said complexes, kits for their preparation. The invention also relates to the use of $^{99m}$Tc radiopharmaceuticals of the invention for SPECT imaging.

13 Claims, 2 Drawing Sheets

Figure 1: Metal Complexes of the present invention.

Figure 2: Ligands of the present invention.

| Ligand Number | R<sup>a</sup> | R<sup>b</sup> |
|---|---|---|
| 1 (prior art) | H | H |
| 2 | H | -COPh |
| 3 | H | -CO-(3-pyridyl) |
| 4 | H | -CO-(4-pyridyl) |
| 5 | H | -COCH$_2$-(piperidinyl) |
| 6 | H | -CO-(imidazolyl) |
| 7 | H | -COCH$_2$-(3-pyridyl) |
| 8 | H | -COCH$_2$-(4-pyridyl) |

Where: Ph = a phenyl group ($C_6H_5$)

SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Tyr Ile Gly Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Pro Asp Ser Gly Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Ile Lys Val Ala Val
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Lys Cys Gln Ala Gly Thr Phe Ala Leu Arg Gly Asp Pro Gln Gly
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Asp Arg Val Tyr Ile His Pro Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: N-Methylglycine

```
<400> SEQUENCE: 6

Xaa Arg Val Tyr Ile His Pro Ile
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 7

Asp Arg Val Tyr Ile His Pro Phe His Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 8

Asn Gln Glu Gln Val Ser Pro Leu Thr Leu Thr Leu Leu Lys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 9

Asn Gln Glu Gln Val Ser Pro Leu Thr Leu Thr Leu Leu Lys Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 10

Asn Gln Glu Ala Val Ser Pro Leu Thr Leu Thr Leu Leu Lys Gly
1               5                   10                  15

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Asn Gln Glu Gln Val Gly
1               5
```

```
<210> SEQ ID NO 12
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 12

Leu Gly Pro Gly Gln Ser Lys Val Ile Gly
1               5                   10
```

TECHNETIUM AND RHENIUM COMPLEXES

CROSS-REFERENCE TO RELATED APPLICATIONS

This application is a continuation of U.S. patent application Ser. No. 11/576,543, filed Apr. 3, 2007, now U.S. Pat. No. 8,022,211, which is a filing under 35 U.S.C. 371 of international application number PCT/GB2005/003806, filed Oct. 4, 2005, which claims priority to application number 0421987.9 filed Oct. 4, 2004, in Great Britain, the entire disclosure of which is hereby incorporated by reference.

TECHNICAL FIELD OF THE INVENTION

The present invention relates to radioactive technetium (Tc) and rhenium (Re) complexes and in particular Tc complexes based on technetium(I) [Tc(I)]. Novel Tc and Re complexes are provided by the present invention as well as a number of novel ligands suitable for use in forming said complexes. The present invention additionally relates to radiopharmaceutical products comprising the novel Tc and Re complexes and kits for the facile preparation of said radiopharmaceuticals. Various uses of these radiopharmaceutical products are also covered by the present invention.

DESCRIPTION OF RELATED ART

The coordination chemistry of Tc and Re plays an important role in the design and synthesis of new radiopharmaceuticals for nuclear medicine. $^{99m}$Tc radiopharmaceuticals have widespread application in the field of nuclear medicine. The physical properties of $^{99m}$Tc make it one of the most desirable radionuclides for external imaging. It is readily available from $^{99}$Mo—$^{99m}$Tc generator systems, has a half life of 6 hours and an optimal energy gamma emission of 140 keV. Re complexes are structural models of the Tc complexes, since the homologous compounds display very similar coordination parameters and physical properties. In addition, Re complexes with the nuclei $^{186}$Re and $^{188}$Re have attractive properties because they are β-emitters with therapeutically-useful energy. A wide range of complexes with these metals have been reported, some of which are currently used in nuclear medicine.

Radiopharmaceuticals based on Tc(I) are desirable due to the fact that the $d^6$-low spin Tc(I) ion is kinetically inert, meaning that such radiopharmaceuticals are extremely stable in vivo. For many years, the only important radiopharmaceutical with Tc in a low oxidation state was $^{99m}$Tc[MIBI]$_6^+$, which is stable in vivo, but not very suitable for chemical substitution. More recently, the development of additional Tc(I) radiopharmaceuticals has been supported by the elucidation of a simple and rapid procedure for the preparation of a reactive Tc(I) moiety, thus facilitating extensive organometallic chemistry. This reactive Tc(I) moiety is [Tc(CO)$_3$(H$_2$O)$_3$]$^+$ and was reported by Alberto et al [J. Am. Chem. Soc. 120 pp 7987-8 (1998)]. The three water molecules bound to the highly inert fac-[Tc(CO$_3$)]$^+$ core can be readily substituted by a number of functional groups to cap one face of the Tc(I) ion and produce stable complexes containing the Tc(CO)$_3$ moiety. For example, Kothari et al [Appl. Rad. Isot. 58 p 543-9 (2003)] demonstrated that an NP$_2$ ligand reacts with [Tc(CO)$_3$(H$_2$O)$_3$]$^+$ to form a stable chelate.

It would be advantageous if the further development of technetium and rhenium radiopharmaceuticals led to the provision of stable metal complexes that are (i) readily coupled to a range of biological vectors, (ii) easily modified to produce both neutral and unipositively charged metal complexes, and (iii) readily derivatised in order to modify both the electronic properties and solubility of the metal complexes.

The tripodal ligand tris(2-pyridyl)methylamine, and some of its derivatives, have been reported by Arnold et al [JCS Dalton Trans. pp 736-46 (2001)]. The paper discloses complexes of the ligands with copper(II) and zinc(II) along with their crystal structures to demonstrate the coordination modes of the various complexes. There is no suggestion by Arnold that the ligands disclosed would be useful in the provision of radioactive technetium and rhenium complexes.

SUMMARY OF THE INVENTION

Novel technetium and rhenium complexes comprising tripodal ligands are provided by the present invention. The tripodal ligands used in the present invention form metal complexes displaying superior properties over prior art metal complexes.

DETAILED DESCRIPTION OF THE INVENTION

In a first aspect, the present invention provides a metal complex of the ligand of Formula I:

(I)

wherein:
the metal is a radioactive isotope of either technetium or rhenium;
$R^1$ is an E group or —CH$_2$(AR$^5$), wherein A is S or O and $R^5$ is H or C$_{1-6}$ alkyl;
$R^2$ and $R^3$ are each independently an E group;
E is an optionally substituted C$_{3-10}$ nitrogen-containing heteroaryl ring; and,
$R^4$ is —(Z)$_q$—Y;
where each Z is independently —CQ$_2$-, —CQ=CQ-, —C≡C—, —CQ$_2$CO$_2$—, —CO$_2$CQ$_2$-, —NQ-, —NQCO—, —CONQ-, —NQ(C=O)NQ-, —NQ(C=S)NQ-, —SO$_2$NQ-, —NQSO$_2$—, —CQ$_2$OCQ$_2$-, —CQ$_2$SCQ$_2$-, —CQ$_2$(NQ)CQ$_2$-, a C$_{4-8}$ cycloheteroalkylene group, a C$_{4-8}$ cycloalkylene group, a C$_{5-12}$ arylene group, or a C$_{3-12}$ heteroarylene group, an amino acid or a monodisperse polyethyleneglycol (PEG) building block; wherein each Q is independently selected from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;
q is an integer of value 0 to 10; and
Y is H, amino, C$_{1-10}$ alkyl, C$_{3-20}$ alkylaryl, C$_{6-14}$ aryl, C$_{3-12}$ heterocycle, C$_{2-10}$ alkoxyalkyl, C$_{1-10}$ hydroxyalkyl, C$_{1-10}$ aminoalkyl, C$_{1-10}$ hydroxyalkyl, C$_{1-10}$ alkoxy, C$_{1-10}$ acyloxy, C$_{6-10}$ aryloxy, or C$_{6-10}$ aroyloxy, or Y is a biological targeting moiety; and wherein not more than three out of a possible five atoms of the ligand are involved in complexation.

A "metal complex" as defined in the present invention means a relatively stable coordination complex wherein the ligand is of Formula I and the central metal is an isotope of Tc or Re. When the metal is an isotope of Tc, it is preferably $^{99m}$Tc or $^{94m}$Tc, in which case the Tc complex of the invention is suitable for in vivo diagnostic imaging by single photon emission computed tomography (SPECT) or positron emission tomography (PET), respectively. When the metal is an isotope of Re, it is preferably $^{186}$Re or $^{188}$Re and therefore suitable for therapy. It is strongly preferred that the metal complex is "resistant to transchelation", i.e. does not readily undergo ligand exchange with other potentially competing ligands for the metal coordination sites.

A "nitrogen-containing heteroaryl ring" of the present invention is any monocyclic or fused aromatic ring structure comprising at least one nitrogen atom, preferably one or two N atoms, most preferably a single N atom. Preferable nitrogen heteroaryl groups of the present invention comprise 5- and 6-membered nitrogen-containing ring structures, examples of which are pyridyl, imidazoyl, pyrimidine, pyrrole, oxazole and pyrazoyl rings plus fused ring analogues thereof such as quinoline. The term "substituted" in the context of nitrogen-containing heteroaryl rings means that one or more organic substituents is attached to the nitrogen-containing heteroaryl ring either at the nitrogen or elsewhere in the ring. Examples of suitable organic substituents include $C_{1-6}$ alkyl, amino, nitro, halo, carboxy, sulphonate and $C_{6-14}$ aryl.

A "biological targeting moiety" is defined in the present invention as a molecule which functions as a means to transport the metal complex to a particular site within the mammalian body, when said metal complex is a radiopharmaceutical. Preferably, the site within the mammalian body is the site of a particular disease state. Suitable biological targeting moieties include: 3-100 mer peptides or peptide analogues which may be linear peptides or cyclic peptides or combinations thereof; monoclonal antibodies or fragments thereof; or enzyme substrates or inhibitors; synthetic receptor-binding compounds; oligonucleotides, or oligo-DNA or oligo-RNA fragments. The biological targeting moiety may be of synthetic or natural origin, but is preferably synthetic. By the term "synthetic" is meant the conventional meaning of the term i.e. man-made as opposed to being isolated from natural sources e.g. from the mammalian body. Such compounds have the advantage that their manufacture and impurity profile can be fully controlled. By the term "cyclic peptide" is meant a sequence of 5 to 15 amino acids in which the two terminal amino acids are bonded together by a covalent bond which may be a peptide or disulphide bond or a synthetic non-peptide bond such as a thioether, phosphodiester, disiloxane or urethane bond.

By the term "amino acid" is meant an L- or D-amino acid, amino acid analogue or amino acid mimetic which may be naturally occurring or of purely synthetic origin, and may be optically pure, i.e. a single enantiomer and hence chiral, or a mixture of enantiomers. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

Suitable peptides for use in the present invention include:
somatostatin, octreotide and analogues,
peptides which bind to the ST receptor, where ST refers to the heat-stable toxin produced by $E.\ coli$ and other micro-organisms;
laminin fragments e.g. YIGSR (SEQ ID NO:1), PDSGR (SEQ ID NO:2), IKVAV (SEQ ID NO:3), LRE and KCQAGTFALRGDPQG (SEQ ID NO:4),
N-formyl peptides for targeting sites of leucocyte accumulation,
Platelet factor 4 (PF4) and fragments thereof,
RGD (Arg-Gly-Asp)-containing peptides, which may e.g. target angiogenesis [R. Pasqualini et al., Nat. Biotechnol. 1997 June; 15(6):542-6]; [E. Ruoslahti, Kidney Int. 1997 May; 51(5):1413-7].
peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
peptides which are substrates or inhibitors of angiotensin, such as:

```
angiotensin II                            (SEQ ID NO: 5)
Asp-Arg-Val-Tyr-Ile-His-Pro-Phe
(E. C. Jorgensen et al, J. Med. Chem., 1979, Vol
22, 9, 1038-1044)[Sar, Ile]

Angiotensin II:                           (SEQ ID NO: 6)
Sar-Arg-Val-Tyr-Ile-His-Pro-Ile
(R. K. Turker et al., Science, 1972, 177, 1203).

Angiotensin I:                            (SEQ ID NO: 7)
Asp-Arg-Val-Tyr-Ile-His-Pro-Phe-His-Leu.
```

Preferably the peptides of the present invention comprise antiplasmin or angiotensin II peptides. Antiplasmin peptides comprise an amino acid sequence taken from the N-terminus of:

(i) $\alpha_2$-antiplasmin,
(SEQ ID NO: 8)
i.e. $NH_2$-Asn-Gln-Glu-Gln-Val-Ser-Pro-Leu-Thr-Leu-Thr-Leu-Leu-Lys-OH or variants of this in which one or more amino acids have been exchanged, added or removed such as:

(SEQ ID NO: 9)
$NH_2$-Asn-Gln-Glu-Gln-Val-Ser-Pro-Leu-Thr-Leu-Thr-Leu-Leu-Lys-Gly-OH, (SEQ ID NO: 10)
$NH_2$-Asn-Gln-Glu-Ala-Val-Ser-Pro-Leu-Thr-Leu-Thr-Leu-Leu-Lys-Gly-OH, $NH_2$-Asn-Gln-Glu-Gln-Val-Gly-OH;       (SEQ ID NO: 11)
or (ii) casein
i.e. Ac-Leu-Gly-Pro-Gly-Gln-Ser-Lys-Val-Ile-Gly.  (SEQ ID NO: 12)

Synthetic peptides of the present invention may be obtained by conventional solid phase synthesis, as described in P. Lloyd-Williams, F. Albericio and E. Girald; *Chemical Approaches to the Synthesis of Peptides and Proteins*, CRC Press, 1997.

Suitable enzyme substrates, antagonists or inhibitors include glucose and glucose analogues such as fluorodeoxyglucose; fatty acids, or elastase, Angiotensin II or metalloproteinase inhibitors. A preferred non-peptide Angiotensin II antagonist is Losartan.

Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The biological targeting moiety is preferably of molecular weight of less than 5000, most preferably less than 4000, ideally less than 3000. Preferred biological targeting moieties are 3-20 mer peptides; or enzyme substrates, antagonists or inhibitors.

The nature of the linker group $(Z)_q$ can also be used to modify the biodistribution of the metal complex when the complex is used as a radiopharmaceutical. Thus, e.g. the introduction of ether groups in $(Z)_q$ will help to minimise plasma protein binding. When $(Z)_q$ comprises a polyethyleneglycol (PEG) building block or a peptide chain of 1 to 10 amino acid residues, the linker group may function to modify the pharmacokinetics and blood clearance rates of the imaging agent in vivo. Such "biomodifier" linker groups may accelerate the clearance of the radiometal imaging agent from background tissue, such as muscle or liver, and/or from the blood, thus giving a better diagnostic image due to less background interference. A biomodifier linker group may also be used to favour a particular route of excretion, e.g. via the kidneys as opposed to via the liver.

When $(Z)_q$ comprises a peptide chain of amino acid residues, the amino acid residues are preferably chosen from glycine, lysine, aspartic acid, glutamic acid or serine. The number of amino acids in the peptide chain is preferably 1 to 10, most preferably 1 to 3.

When $(Z)_q$ comprises a PEG moiety, it preferably comprises a group of formula $(-OCH_2CH_2O-)_w$ where w is an integer of value 3 to 25. The integer w is preferably 6 to 22. An especially preferred PEG-containing $(Z)_q$ group is a unit derived from polymerisation of the monodisperse PEG-like structure, 17-amino-5-oxo-6-aza-3,9,12,15-tetraoxaheptadecanoic acid Formula Ia:

(Ia)

wherein p is an integer from 1 to 10.

Each E group is preferably an optionally substituted $C_{3-6}$ nitrogen-containing heteroaryl ring. Preferred E groups are selected from pyridyl, imidazoyl and pyrazoyl, with 2-pyridyl being especially preferred.

A preferred embodiment of Formula I is where each of $R^1$, $R^2$ and $R^3$ are E groups, with the preferred E groups as described above. In this embodiment $R^1$, $R^2$ and $R^3$ are preferably each the same E group, which gives a symmetric tripodal ligand, and are most preferably each 2-pyridyl.

$R^4$ is preferably a functionalised acyl substituent of formula $-NH(CO)-(Z)_x-Y$, where x is an integer of value 0 to 9. Such acyl substituents are preferred since they permit facile functionalisation of the ligand at the $R^4$ position, and the acyl group does not compete with the donor atoms of the $R^1$, $R^2$ and $R^3$ groups. Such competition can be a problem when $R^4$ is amino (i.e. q=0 and Y is amino), since the amine group can also form a favoured 5-ring chelate upon metal coordination.

In a preferred metal complex of the ligand of Formula I, the metal co-ordinates via the A atom of the $R^1$ group and the nitrogen atom of the heteroaryl rings of the E groups, such that the ligand acts as a tripodal chelating agent.

The preferred embodiments of the first aspect of the invention outlined above are metal complexes with an oxidation state of +1. These complexes are of particular interest when the metal is technetium because of the low kinetic inertness of the $d^6$-low spin Tc(I) ion. Furthermore, it is possible to derivatise the ligand with a range of biological targeting molecules allowing use of the resulting complexes in a range of applications. A key advantage of the synthetic protocol is that the tripodal ligands can be readily modified to produce both neutral and charged complexes. Thus, in Formula (I), when $R^1$ is $-CH_2(AR^5)$, A is preferably S. When $R^1$ is $-CH_2(SR^5)$, and an uncharged ligand is desired, $R^5$ is preferably $C_{1-3}$ alkyl and is most preferably $-CH_2(SCH_3)$, $-CH_2(SC_2H_5)$ or $-CH_2(SC_3H_7)$. When $R^1$ is $-CH_2(SR^5)$, and a negatively charged ligand is desired, $R^5$ is preferably H, i.e. $R^1$ is $-CH_2SH$.

The radiometal complexes of the present invention may be prepared by reaction of a solution of the radiometal in the appropriate oxidation state with the ligand of Formula I at the appropriate pH. The solution may preferably contain a ligand which complexes weakly to the metal (such as gluconate or citrate) i.e. the radiometal complex is prepared by ligand exchange or transchelation. Such conditions are useful to suppress undesirable side reactions such as hydrolysis of the metal ion. When the radiometal ion is $^{99m}$Tc, the usual starting material is sodium pertechnetate from a $^{99}$Mo generator. Technetium is present in $^{99m}$Tc-pertechnetate in the Tc(VII) oxidation state, which is relatively unreactive. The preparation of technetium complexes of lower oxidation state Tc(I) to Tc(V) therefore usually requires the addition of a suitable pharmaceutically acceptable reducing agent such as sodium dithionite, sodium bisulphite, ascorbic acid, formamidine sulphinic acid, stannous ion, Fe(II) or Cu(I), to facilitate complexation. The pharmaceutically acceptable reducing agent is preferably a stannous salt, most preferably stannous chloride, stannous fluoride or stannous tartrate.

Further details on the preparation of $^{99m}$Tc metal complexes are given by Mease et al [Semin. Nucl. Med., 31(4), 278-285 (2001)]. Further details on the preparation of radioactive rhenium metal complexes are given by Hashimoto et al [Chapter 9 pages 275-291 in "Technetium and Rhenium: Their Chemistry and its Applications", Yoshihara and Omori (Eds), Springer, Berlin (1996)]. A preferred method of preparation of $^{99m}$Tc complexes of the present invention is via the use of lyophilised kits, as described in the fifth embodiment below.

In a second aspect, the present invention provides a metal complex of Formula II:

$$[LMX_3]^n \qquad (II)$$

where L is a ligand of Formula I as defined for the first embodiment,

M is a radioactive isotope of technetium or rhenium;

X is selected from CO, halogen, phosphine or isonitrile, and n is the charge on the metal complex, and can be −1, 0, +1 or +2.

When X is an isonitrile, it is suitably a monodentate isonitrile. When all three X groups are phosphines, the three X donor atoms may be made up of three monodentate phosphines, a single tridentate phosphine or a mixture of a monodentate and a bidentate phosphine.

The charge on the metal complex (n) of Formula II will depend on the donor atoms present in the ligand (L) and the identity of X. Thus, e.g. when X is CO, phosphine or isonitrile these are neutral donors and do not affect the charge. When X is halogen, however, these are negatively charged donors. When $R^1$ of the ligand of Formula I is —$CH_2SH$ it is anticipated that metal complexation occurs via a thiolate anion, i.e. the thiol is deprotonated so that the ligand carries a single negative charge.

Metal complexes of Formula II can be prepared as described for the first embodiment (above), plus the methods of Barrera et al [Inorg. Chem., 35, 335-341 (1996)].

A preferred X group of Formula II is CO (i.e. a carbonyl group). This corresponds to the charged complex of Formula IIa and the neutral complex of Formula IIb as described below:

$$[LM(CO)_3]^n \quad\quad (IIa)$$

where:
M is as defined in Formula II;
L is a ligand of Formula I as defined above, wherein:
$R^1$ is an E group or is —$CH_2(AR^5)$ wherein $R^5$ is $C_{1-6}$ alkyl;
$R^4$ is amino or —$(Z)_q$—Y wherein Z, q and Y are as defined in claim 1.
n is +1 or +2.

Preferred metal complexes of Formula IIa comprise the preferred ligands as described for the first embodiment (above). Preferably n is +1. Preferably, $R^1$, $R^2$ and $R^3$ in Formula IIa are each 2-pyridyl, and $R^4$ is a functionalised acyl substituent of formula —NH(CO)—$(Z)_x$—Y, where x is an integer of value 0 to 9 as described above for Formula II. When Y is not a biological targeting moiety, Y is preferably amino, phenyl, pyridyl, piperidinyl, or imidazoyl. Most preferably, $R^4$ is —NH(CO)Ph, —NH(CO)($CH_2)_3$—(CO)NHCH$_2$Ph,
—NH(CO)(3-pyridyl), —NH(CO)(4-pyridyl), —NH(CO)$CH_2$-piperidinyl, —NH(CO)NH$_2$, or
—NH(CO)(2,4-imidazoyl).

A further preferred metal complex of Formula II is a neutral complex of Formula IIb:

$$LM(CO)_3 \quad\quad (IIb)$$

wherein:
M is as defined in Formula II;
L is a ligand of Formula I wherein $R^1$ is —$CH_2SH$ or —$CH_2OH$;
$R^2$ and $R^3$ and $R^4$ are as defined for Formula I.
Preferably, $R^1$ in Formula IIb is —$CH_2SH$ and $R^2$ and $R^3$ of L are each 2-pyridyl.

The metal complex is neutral as a result of deprotonation of —$CH_2SH$ or —$CH_2OH$ upon coordination to the metal.

In Formulae II, IIa and IIb M is preferably $^{94m}Tc$, $^{99m}Tc$, $^{186}Re$ or $^{186}Re$ and is most preferably $^{99m}Tc$.

Where each X is CO and M is $^{99m}Tc$, the complexes of the second aspect of the invention can be conveniently prepared from the $^{99m}Tc(CO)_3((H_2O)_3^+$ precursor as described by Schibli et al [Bioconj. Chem., 11, p 345-351 (2000)] and Kothari et al [Appl. Rad. Isotop., 58, 543-549 (2003)]. The three water molecules of the precursor can be easily replaced by donor atoms of the ligand of Formula I in order to form Tc complexes of the invention. The $^{99m}Tc(CO_3)(H_2O)_3^+$ precursor for non-clinical use may also be obtained using an Isolink™ kit (Mallinckrodt, Petten, Netherlands). Subsequent reaction of [$^{99m}Tc(CO_3)(H_2O)_3]^+$ with a ligand of the invention results in the formation of a $^{99m}Tc$ complex of the invention. The corresponding rhenium metal complexes can be prepared by the methods of Pietzsch et al [Bioconj. Chem., 11, p 414-424 (2000)].

Figure 1:
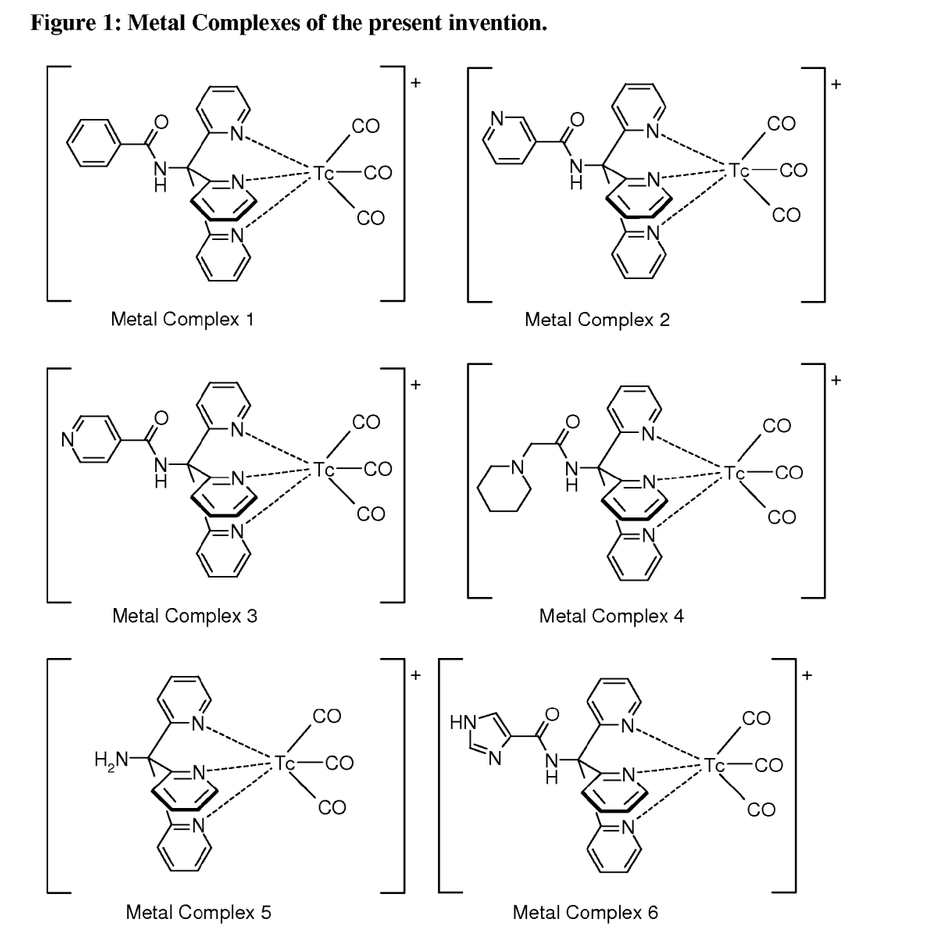
FIG. 1 shows several metal complexes of the invention.

A number of examples of metal complexes of Formula IIa are illustrated in FIG. 1.

In a third aspect, the present invention provides a ligand as defined in Formula I, with the proviso that when $R^1$ is —$CH_2SCH_3$ or comprises a 2-pyridyl or 2-quinoline ring, and $R^2$ and $R^3$ each comprise a 2-pyridyl ring, then $R^4$ is not H, —$CH_2OH$, $C_{1-4}$ alkyl, —$NH_2$ or
—NH(CO)$R^x$, where $R^x$ is $C_{1-12}$ alkyl, $C_{1-4}$ carboxyalkyl or —$C_6H_4SO_3H$.

One preferred class of ligand of the third embodiment is those in which $R^1$ is —$CH_2SH$ or
—$CH_2OH$. More preferred such ligands are those wherein either (i) $R^1$ is —$CH_2SH$, and $R^2$ and $R^3$ each comprise a 2-pyridyl group; or (ii) wherein $R^1$, $R^2$ and $R^3$ each comprise a 2-pyridyl group. Most preferred ligands are those wherein $R^1$, $R^2$ and $R^3$ each comprise a 2-pyridyl group.

Preferred $R^4$ groups of the third embodiment are those in which Y is either —$(CH_2)_mNH_2$ where m is an integer of value 1 to 6, preferably 2 to 4; or is a biological targeting moiety, i.e. conjugates of the ligands with a biological targeting moiety. Additional preferred $R^4$ groups are those wherein Y is amino-substituted phenyl, pyridyl, piperidyl, or imidazoyl.

The ligands of the present invention can be prepared by the method of Arnold et al [JCS Dalton Trans., 736-746 (2001)]. When $R^1$, $R^2$ and $R^3$ each comprise a 2-pyridyl group and $R^4$ is H, the bridgehead proton ($R^4$ group) can be deprotonated with butyl lithium, and subsequently alkylated with alkyl halides as is taught by Kodera et al [Inorg. Chem., 42, 1193-1203 (2003)]. Functionalised versions thereof, including conjugates with biological targeting moieties can also be prepared via the bifunctional chelate approach. Thus, it is well known to prepare ligands or chelating agents which have attached thereto a functional group ("bifunctional linkers" or "bifunctional chelates" respectively). Functional groups that have been attached include: amine, thiocyanate, maleimide and active esters such as N-hydroxysuccinimide or pentafluorophenol. Ligand 1 of the present invention is an example of an amine-functionalised bifunctional chelate. Bifunctional chelates suitable for complexation to a technetium or rhenium tricarbonyl core are described by Stichelberger et. al [Nucl. Med. Biol., 30, 465-470 (2003)]. Such bifunctional chelates can be reacted with suitable functional groups on the biological targeting moieties to form the desired conjugate. Suitable functional groups on the compounds to be conjugated include:

carboxyls (for amide bond formation with an amine-functionalised bifunctional chelator);

amines (for amide bond formation with an carboxyl- or active ester-functionalised bifunctional chelator);

halogens, mesylates and tosylates (for N-alkylation of an amine-functionalised bifunctional chelator) and thiols (for reaction with a maleimide-functionalised bifunctional chelator).

Examples 1 to 4 provide further syntheses of ligands of the invention.

In a fourth aspect, the present invention provides a radiopharmaceutical comprising the metal complex of the invention in any of the aspects and embodiments described above together with a biocompatible carrier in a form suitable for mammalian, especially human, administration. The "biocompatible carrier" is a fluid, especially a liquid, in which the imaging agent can be suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like).

Such radiopharmaceuticals are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, and are therefore preferably a disposable or other syringe suitable for clinical use. The pre-filled syringe may optionally be provided with a syringe shield to protect the operator from radioactive dose. Suitable such radiopharmaceutical syringe shields are known in the art and preferably comprise either lead or tungsten.

Preferred radiopharmaceuticals of the present invention comprise the technetium radioisotopes $^{99m}$Tc or $^{94m}$Tc, most preferably $^{99m}$Tc. When the technetium isotope is $^{99m}$Tc, a radioactivity content suitable for a diagnostic imaging radiopharmaceutical is in the range 180 to 1500 MBq of $^{99m}$Tc, depending on the site to be imaged in vivo, the uptake and the target to background ratio.

Where X of Formula II is CO, the $^{99m}$Tc radiopharmaceuticals of the present invention may be prepared by first preparing $[^{99m}Tc(CO_3)(H_2O)_3]^+$ as described above. Subsequent reaction of $[^{99m}Tc(CO_3)(H_2O)_3]^+$ with a ligand of the invention results in the formation of a $^{99m}$Tc complex of the invention. Both steps are carried under sterile conditions or terminal sterilisation is employed.

In a fifth aspect, the present invention provides a non-radioactive kit for the preparation of the radiopharmaceutical composition described above, which comprises the ligand of Formula (I), as defined in the first embodiment. When the radiometal is $^{99m}$Tc, the kit suitably further comprises a biocompatible reductant. Such kits are designed to give sterile radiopharmaceutical products suitable for human administration, e.g. via direct injection into the bloodstream. For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (e.g. a septum-sealed vial) containing the ligand or chelator conjugate in either free base or acid salt form, together with a biocompatible reductant such as sodium dithionite, sodium bisulphite, ascorbic acid, formamidine sulphinic acid, stannous ion, Fe(II) or Cu(I). The biocompatible reductant is preferably a stannous salt such as stannous chloride or stannous tartrate. Alternatively, the kit may optionally contain a metal complex which, upon addition of the radiometal, undergoes transmetallation (i.e. metal exchange) giving the desired product.

The non-radioactive kits may optionally further comprise additional components such as a transchelator, radioprotectant, antimicrobial preservative, pH-adjusting agent or filler. The "transchelator" is a compound which reacts rapidly to form a weak complex with technetium, then is displaced by the ligand. This minimises the risk of formation of reduced hydrolysed technetium (RHT) due to rapid reduction of pertechnetate competing with technetium complexation. Suitable such transchelators are salts of a weak organic acid, i.e. an organic acid having a pKa in the range 3 to 7, with a biocompatible cation. Suitable such weak organic acids are acetic acid, citric acid, tartaric acid, gluconic acid, glucoheptonic acid, benzoic acid, phenols or phosphonic acids. Hence, suitable salts are acetates, citrates, tartrates, gluconates, glucoheptonates, benzoates, phenolates or phosphonates. Preferred such salts are tartrates, gluconates, glucoheptonates, benzoates, or phosphonates, most preferably phosphonates, most especially diphosphonates. A preferred such transchelator is a salt of MDP, i.e. methylenediphosphonic acid, with a biocompatible cation.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition post-reconstitution, i.e. in the radioactive diagnostic product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [i.e. tris (hydroxymethyl)aminomethane], and pharmaceutically acceptable bases such as sodium carbonate, sodium bicarbonate or mixtures thereof. When the conjugate is employed in acid salt form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

In a sixth aspect, the present invention relates to use of the radiopharmaceutical of the invention, wherein the radiometal is a gamma emitter, for SPECT imaging. Following administration of the radiopharmaceutical to a subject, the distribution of the radiopharmaceutical within said subject is detected by means of a gamma camera, which produces an image indicative of said distribution.

Figure 2:
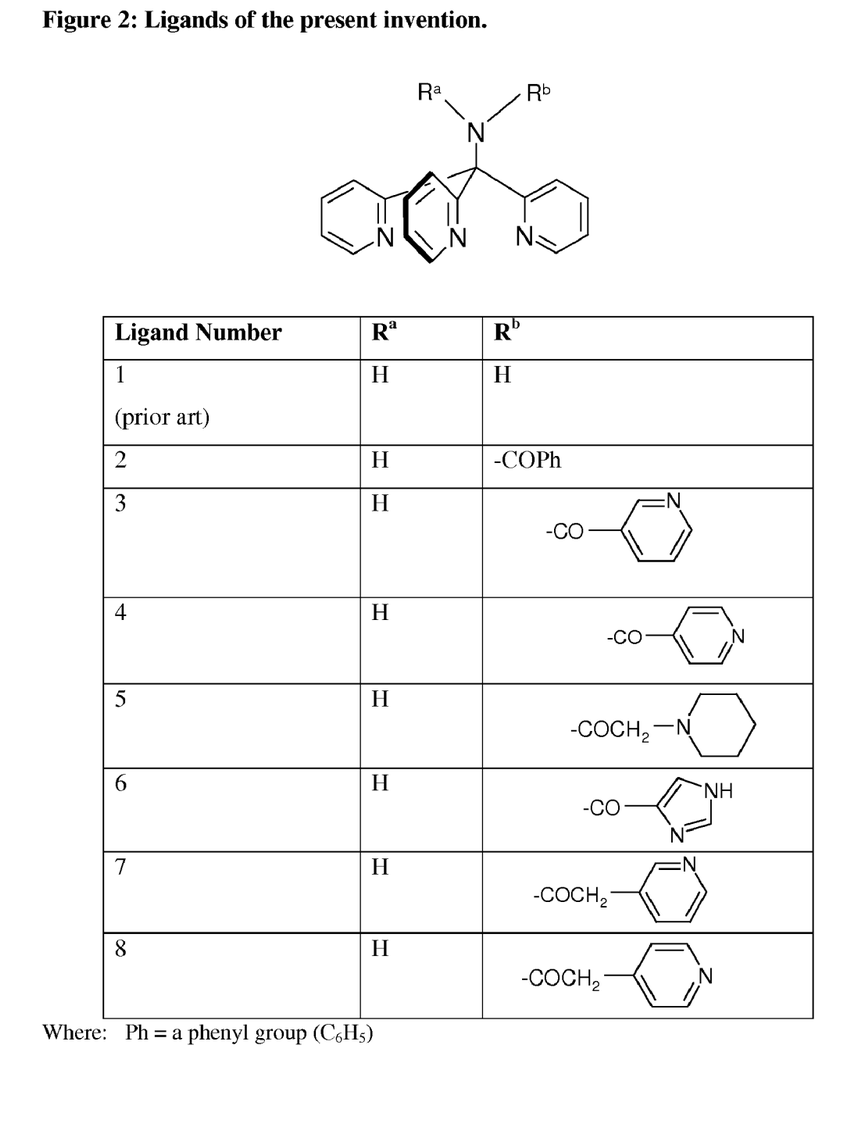
FIG. 2 summarises the chemical structures of the ligands of the Examples.

The invention is illustrated by the non-limiting Examples detailed below. Examples 1 to 4 provide the syntheses of Ligands 2 to 8. Example 5 provides a method of preparation of a $^{99m}$Tc-tricarbonyl complex of Ligand 6. The radiochemical purity (RCP) was 98%. Example 4 provides the method of preparation of the $^{99m}$Tc-tricarbonyl complexes of Ligands 1, 2, 4, 5 and 6.

EXPERIMENTAL EXAMPLES

Ligand 1 [i.e. 1,1,1-tris(pyridin-2-yl)methylamine] was prepared by the method of Arnold et al [JCS Dalton Trans., 736-746 (2001)].

Example 1

Synthesis of Ligand 2

Benzoic anhydride (280 mg, 1.24 mmol) was added in one portion to a stirred solution of Ligand 1 (250 mg 0.95 mmol) in $CH_2Cl_2$ (2 ml) at room temperature. Stirring was continued for 24 hours and the reaction mixture diluted with $CH_2Cl_2$ (18 ml). This solution was washed with saturated sodium bicarbonate (20 ml×2) and water (20 ml×2), and then dried ($MgSO_4$), filtered and the solvent evaporated to leave a yellow residue. Recrystallisation of this material from a $CH_2Cl_2$/pentane mixture gave the product (180 mg, 52%) as a yellow powder, m p 233-234° C.

$^1$H NMR ($CDCl_3$): $\delta_H$ 7.10-7.17 (3H, m, 5-H), 7.41-7.51 (3H, m, 4-H), 7.59-7.64 (6H, m, 3-H [×2], meta-H [×2], para-H), 8.0 (2H, dd, J=7 and 2 Hz, ortho-H [×2]), 8.53 (3H, br d, J=5 Hz, 6-H [×3]).

Mass Spec (ES) m/e:—Calculated for $C_{23}H_{19}N_4O$ (M+H), 367. Found 367.

Example 2

Synthesis of Ligands 3 and 4

Thionyl chloride (5.0 g, 42 mmol) and nicotinic acid (620 mg, 5.0 mmol) were heated under reflux for 3 hours and the excess reagent then removed under reduced pressure to leave a white residue. This residue was co-evaporated with toluene (25 ml×2) under reduced pressure to leave a white powder. This resulting solid was added in 50 mg portions with stirring to a solution of Ligand 1 (250 mg, 0.95 mmol) in $CH_2Cl_2$ (10 ml) containing triethylamine (1.10 g, 10.0 mmol). After stirring at room temperature for 16 hours the solution was washed with water (20 ml×2), dried ($MgSO_4$), filtered and the solvent removed under reduced pressure to leave a dark brown residue. This residue was purified by chromatography on silica gel eluting with a $CH_2Cl_2$/MeOH mixture (20:1). The required product was isolated as a yellow solid ($r_f$=0.25) which was recrystallised from $CH_2Cl_2$/Pentane to give a pale yellow powder (Yield 210 mg, 60.0%), m p 206-207° C.

$^1$H NMR ($CDCl_3$): $\delta_H$ 7.14 (3H, dt, J=5.0 and 2.7 Hz, 5-H [×3], 7.35 (1H, dd, J=8.0 and 5.0 Hz, 5'-H), 7.58-7.61 (3H, m 4-H [×3]), 7.62 (3H, dt, J=8.2 and 1.5 Hz, 3-H [×3]), 8.23 (1H, dt, J=8.0 and 2.0 Hz, 4'-H), 8.51 (3H, br d, J=5 Hz, 6-H [×3]), 8.71 (1H, dd, J=5.0 and 1.5 Hz, 6'-H), 9.25 (1H, d, J=2.0 Hz, 2'-H), 10.4 (1H, s, NH).

Mass Spec (ES) m/e: Calculated for $C_{22}H_{18}N_5O$ (M+H), 368. Found 368.

Ligand 4 was prepared in an analogous manner from isonicotinic acid as the starting material, giving a pale yellow powder (140 mg, 40.0%). m p 183-185° C.

$^1$H NMR ($CDCl_3$): $\delta_H$ 7.15 (3H, dt, J=5.0 and 1.5 Hz, 5-H [×3], 7.57-7.66 (6H, m 4-H [×3], 3-H [×3], 7.80 (2H, d, J=5.9 Hz, 2'-H, 6'-H) 8.51 (3H, d, J=5 Hz, 6-H [×3], 8.74 (2H, d, J=5.9 Hz, 3'-H, 5'-H), 10.45 (1H, bs, NH).

Mass Spec (ES) m/e:—Calculated for $C_{22}H_{18}N_5O$ (M+H), 368. Found 368.

Example 3

Synthesis of Ligand 5

Step (a): Ethyl 2-(piperidin-1-yl)-acetate

Ethyl bromoacetate (8.5 g, 50.9 mmol) was added dropwise to a stirred solution of piperidine (4.3 g, 50.5 mmol) and triethylamine (5.5 g, 54.4 mmol) in chloroform (20 ml) at such a rate as to maintain a gentle reflux. After the addition was complete stirring was continued for 2 hours and the reaction mixture washed with water (20 ml×3). The chloroform layer was dried ($MgSO_4$) filtered and the solvent evaporated to leave a yellow oil. This oil was passed through a short column of silica eluting with a $CH_2Cl_2$/Pet Ether 40:60 mixture (1:1). Removal of the solvent from the resulting solution gave the required product as a pale yellow oil (Yield 5.5 g, 64%).

$^1$H NMR ($CDCl_3$):—$\delta_H$ 1.20 (3H, t, J=7.0 Hz, $CH_3$), 1.40 (2H, m, 4'-H), 1.55 (4H, m, 3'-H 5'-H), 2.42 (4H, m, 2'-H 6'-H), 3.10 (2H, s, $NCH_2CO$) 4.10 (2H, q, J=7 Hz, $OCH_2$).

Step (b): Piperidin-1-yl acetic acid hydrochloride

Ethyl 2-(piperidin-1-yl)-acetate (5.5 g, 32.2 mmol), water (12 ml) and c HCl (3 ml) were heated under reflux for 20 hours. Volatile components were evaporated under reduced pressure to leave an off white solid. This solid was co-evaporated with toluene (50 ml×3) and dried in vacuo to give an off white powder (Yield 4.8 g, 83%).

$^1$H NMR ($D_2O$); —$\delta_H$ 1.42-1.46 (1H, m, 4'-H), 1.73-1.86 (5H, m, 2'-H 3'-H 4'-H), 2.97-3.05 (2H, m, 2'-H 6'-H), 3.52-3.57 (2H, m, 2'-H 6'-H), 4.02 (2H, s, $NCH_2CO$).

Step (c): 2-(Piperidin-1-yl)-N-[1,1,1-tris(pyridyl-2-yl)methyl]-acetamide

Lithium hydroxide (85 mg, 3.5 mmol) and piperidin-1-yl acetic acid hydrochloride (300 mg, 1.68 mmol) were dissolved in methanol (10 ml) to give a colourless solution. The methanol was then was removed under reduced pressure and the colourless solid co-evaporated with toluene until a free flowing powder remained. To this lithium salt was added dry DMF (10 ml), Ligand 1 (250 mg, 0.95 mmol), Pybop (510 mg, 0.98 mmol) and the mixture warmed until a clear solution was obtained. Heat was removed and stirring continued for 16 hours. Volatile components were removed under reduced pressure to leave an orange residue which was dissolved in $CH_2Cl_2$ (20 ml) and washed with water (20 ml×3). The organic layer was dried ($MgSO_4$), filtered and the solvent evaporated to leave an orange oil. This residue was purified by chromatography on silica gel eluting with a $CH_3CN$/MeOH mixture (200:5). The required product was isolated ($r_f$=0.2) as a pale yellow oil which solidifies on standing (100 mg 27%). m p 123-125° C.

$^1$H NMR (CDCl$_3$):—δ 1.45-1.50 (2H, m, 4'-H)), 1.65-1.63 (4H, m, 3'-H 5'-H), 2.54-2.57 (4H, m, 2'-H 6'-H), 3.01 (2H, s, NCH$_2$CO), 7.12 (3H, ddd, J=7.5, 5.0 and 1.0 Hz, 5-H, [×3]) 7.46-7.50 (3H, m, 3-H [×3]), 7.60 (3H, dt, J=7.5 and 5.0 Hz, 4-H [×3]), 8.50-8.53 (3H, m, 6-H [×3]), 10.61 (1H, s, NH).

Mass Spec (ES) m/e:—Calculated for C$_{23}$H$_{26}$N$_5$O (M+H), 388 Found 388

Example 4

Synthesis of Ligands 6, 7 and 8

1H-Imidazole-4-carboxylic acid (200 mg, 1.8 mmol) and lithium hydroxide (45 mg, 1.9 mmol) were dissolved in methanol (10 ml) to give a clear solution. Volatile components were removed under reduced pressure and the residue co-evaporated with toluene until a free flowing powder was obtained. To the lithium salt was added dry DMF (10 ml), Ligand 1 (250 mg, 0.95 mmol) and Pybop (510 mg, 0.98 mmol). The mixture was warmed until a clear orange solution was obtained. Heat was then removed and the solution stirred for 16 hours. The solvent was removed by rotary evaporation to leave a viscous orange residue which was purified by chromatography on silica gel eluting with CH$_3$CN/MeOH (95:5). The title compound (100 mg, 29%) was isolated ($r_f$=0.3) as a white powder m p>250° C.

$^1$H NMR (d$^6$ DMSO):—δ$_H$ 5.76 (1H, s, NH imid), 7.23-7.28 (3H, m, 5-H [×3], 7.44-7.47 (3H, m, 3-H [×3]), 7.53 (1H, s, C—H, imid), 7.72 (3H, bt, J=7 Hz, 4-H [×3], 7.82 (1H, s, C—H imid), 8.50 (3H, m, 6-H [×3]), 10.46 (1H, s, NH).

Mass Spec (ES) m/e:—Calculated for C$_{20}$H$_{17}$N$_6$O (M+H), 357. Found 357.

Ligand 7 was prepared in an analogous manner from 4-pyridylacetic acid hydrochloride giving a colourless powder (Yield 40 mg, 11%), m pt 134-135° C.

$^1$H NMR (CDCl$_3$): δ$_H$ 3.70 (2H, s, CH$_2$), 7.13 (3H, m, 5-H [×3], 7.26 (2H, d, J=5.0 3-H, 5-H), 7.43 (3H, d, J=6 Hz 3-H [×3], 7.57 (3H, t, J=6 Hz 4-H [×3], 8.47 (3H, d, J=5 Hz, 6-H [×3], 8.53 (2H, d, J=5.0 Hz, 2-H, 6-H)), 9.49 (1H, bs, NH).

Mass Spec (ES) m/e:—Calculated for C$_{23}$H$_{20}$N$_5$O (M+H), 382. Found 382

Ligand 8 was prepared in an analogous manner from 3-Pyridyl acetic acid hydrochloride giving a fawn coloured powder (180 mg, 54%), m p 165-166° C.

$^1$H NMR (CDCl$_3$): δ$_H$ 3.68 (2H, s, CH$_2$) 7.08 (3H, ddd, J=7.5, 5.0 and 1.0 Hz, 5-H [×3], 7.19 (1H dd, J=7.5 and 5.0 Hz 5'-H), 7.43 (3H, m, 3-H [×3]), 7.53 (3H, dt, J=7.5 and 5.0 4-H [×3], 7.64 (1H, bd, J=7.5 Hz 4'-H), 8.43 (3H, m, 6-H [×3], 8.46 (1H, dd, J=7.5 and 1.5 Hz, 6'-H), 8.56 (1H, d, J=1.5 Hz, 2'-H), 9.49 (1H, s, NH).

Mass Spec (ES) m/e:—Calculated for C$_{23}$H$_{20}$N$_5$O (M+H), 382. Found 382.

Example 5

Preparation of the $^{99m}$Tc Tricarbonyl Complex of Ligand 6

1 mL of TcO$_4^-$ eluted from a generator was added to a Tc-carbonyl kit (Isolink™, Mallinckrodt, Petten, Netherlands). Activity was measured at 983 MBq. Approximately 4 mL headspace was removed from the vial, which was then heated to approx 100° C. for 30 minutes. The vial was allowed to cool, and the pressure was equalised using bleed needle. 50-100 ug of Ligand 6 was added before removal of 4 mL headspace. The vial was heated to approx 100° C. for 30 minutes and then allowed to cool, before equalising the pressure of the vial using bleed needle. The pH was measured to be approximately 11.5 and the radiochemical purity (RCP) determined by high performance liquid chromatography (HPLC) was 98%.

Two HPLC methods were used as follows:

Method A

Solvent A=0.1% TFA in water, solvent B=0.1% TFA in acetonitrile

Method B

Solvent A=0.2% 880 ammonia solution, solvent B=acetonitrile

For both methods, the following gradient was used:

| Time (min) | % B |
|---|---|
| 0 | 20 |
| 5 | 45 |
| 14 | 45 |
| 15 | 100 |
| 19 | 100 |
| 21 | 20 |
| 23 | 20 |

Example 6

Preparation of $^{99m}$Tc Tricarbonyl Complexes of Ligands 1, 2, 4, 5 and 6

1 mL TcO$_4^-$ eluted from a generator was added to a Tc-carbonyl kit (Isolink™, Mallinckrodt, Petten, Netherlands). The activity was measured as 2.88 Gq. Approximately 4 mL headspace was removed from the vial, which was then heated to approximately 100° C. for 30 minutes. The vial was allowed to cool, and the pressure equalised using bleed needle.

50-100 ug (in 0.1 mL MeOH) of Ligand was added to a nitrogen filled vial, followed by 0.7 mL 0.4M phosphate buffer (pH approx 7.5). 0.2 mL Tc(CO)$_3$(H$_2$O)$_3$]$^+$ prepared from the kit was then added and the activity was measured as 593 Mq. The vial was heated to approx 100° C. for 30 minutes before being allowed to cool, and the pressure equalised using a bleed needle. The pH was approximately 8.5 and the RCP for each complex as determined by HPLC (described in Example 5) was as follows:

| $^{99m}$Tc Complex | RCP (%) |
|---|---|
| Ligand 1 | 94 |
| Ligand 2 | 65 |
| Ligand 4 | 40 |
| Ligand 5 | 87 |
| Ligand 6 | 90 |

The invention claimed is:

1. A metal complex of a ligand of Formula I:

(I)

wherein:
the metal is a radioactive isotope of either technetium or rhenium;
$R^1$-$R^3$ are independently selected from pyridyl, imidazoyl and pyrazoyl; and,
$R^4$ is —NH(CO)Ph, —NH(CO)(CH$_2$)$_3$—(CO)NHCH$_2$Ph, —NH(CO)(3-pyridyl), —NH(CO)(4-pyridyl), —NH(CO)CH$_2$-piperidinyl, —NH(CO)NH$_2$, or —NH(CO)(2,4-imidazoyl);
and wherein not more than three out of a possible five atoms of the ligand are involved in complexation.

2. The metal complex of claim 1 wherein $R^1$, $R^2$ and $R^3$ are each pyridyl.

3. The metal complex of claim 1 wherein $R^1$, $R^2$ and $R^3$ are each 2-pyridyl.

4. The metal complex of claim 1 wherein the metal is a radioactive isotope of technetium.

5. The metal complex of claim 4 wherein the radioactive isotope of technetium is $^{99m}$Tc.

6. A metal complex of Formula II:

[LMX$_3$]$^n$ (II)

wherein:
L is a ligand of Formula I as defined in claim 1;
M is the radioactive isotope of technetium or rhenium;
X is selected from CO, halogen, phosphine, or isonitrile; and,
n is the charge on the metal complex, and is −1, 0, +1 or +2.

7. The metal complex of claim 6 which is of Formula IIa:

[LM(CO)$_3$]$^n$ (IIa)

wherein L is a ligand of Formula I as defined in claim 1, wherein:
$R^1$, $R^2$ and $R^3$ are each 2-pyridyl, and n is +1 or +2.

8. The metal complex of claim 6 wherein M is a radioactive isotope of technetium.

9. The metal complex of claim 8 wherein the radioactive isotope of technetium is $^{99m}$Tc.

10. A ligand of Formula I:

(I)

wherein:
$R^1$-$R^3$ are independently selected from pyridyl, imidazoyl, and pyrazoyl; and $R^4$ is —NH(CO)Ph, —NH(CO)(CH$_2$)$_3$—(CO)NHCH$_2$Ph, —NH(CO)(3-pyridyl), —NH(CO)(4-pyridyl), —NH(CO)CH$_2$-piperidinyl, —NH(CO)NH$_2$, or —NH(CO)(2,4-imidazoyl).

11. The ligand of claim 10 wherein $R^1$, $R^2$ and $R^3$ each comprise a 2-pyridyl group.

12. A radiopharmaceutical comprising the metal complex of claim 1.

13. A kit for the preparation of the radiopharmaceutical of claim 12 comprising a ligand of Formula I:

(I)

wherein:
$R^1$-$R^3$ are independently selected from pyridyl, imidazoyl, and pyrazoyl; and $R^4$ is —NH(CO)Ph, —NH(CO)(CH$_2$)$_3$—(CO)NHCH$_2$Ph, —NH(CO)(3-pyridyl), —NH(CO)(4-pyridyl), —NH(CO)CH$_2$-piperidinyl, —NH(CO)NH$_2$, or —NH(CO)(2,4-imidazoyl).

* * * * *